United States Patent [19]
Zimmer et al.

[11] Patent Number: 6,013,809
[45] Date of Patent: Jan. 11, 2000

[54] SUBSTITUTED HETEROCYCLIC BENZOCYCLOALKENES AND THE USE THEREOF AS SUBSTANCES HAVING AN ANALGESIC EFFECT

[75] Inventors: Oswald Zimmer; Wolfgang Strassburger, both of Wuerselen; Claudia Puetz, Dueren; Werner Englberger, Stolberg; Babette-Yvonne Koegel, Langerwehe-Hamich, all of Germany

[73] Assignee: Gruenenthal GmbH, Aachen, Germany

[21] Appl. No.: 09/208,990

[22] Filed: Dec. 11, 1998

[30] Foreign Application Priority Data

Dec. 13, 1997 [DE] Germany .......................... 197 55 480

[51] Int. Cl.$^7$ ...................... C07D 337/00; C07D 335/04; C07D 335/02; C07D 313/00; C07D 311/04

[52] U.S. Cl. .................. 549/9; 549/23; 549/28; 549/355; 549/398

[58] Field of Search .................. 549/9, 23, 28, 549/355, 398

[56] References Cited

U.S. PATENT DOCUMENTS

3,444,176  5/1969  Mohrbacher.
5,482,967  1/1996  Natsugari et al. ...................... 514/457

OTHER PUBLICATIONS

K. Sindelar et al., "Neurotropic and Psychotropic Compounds, XXIX, Derivatives of 2,3,4,5–Tetrahydro–1–Benzothiepin," Collection of Czechoslovak Chemical Communications, vol. 33, No. 12, 1968, pp. 4315–4327.

M. Protiva et al., "Benzocycloheptenes and Heterocyclic Analogues as Potential Drugs, II, Amines of 8–Chloro–2,3, 4,5–Tetrahydro–1–Benzoxepin Series," Collection of Czechoslovak Chemical Communications, vol. 37, No. 3, 1972, pp. 868–886.

Chemical Abstracts, vol. 74, No. 19, May 10, 1971, CS–133727, M. Protiva et al., Oct. 15, 1969.

Patent Abstracts of Japan, vol. 10, No. 318, Oct. 19, 1986, JP 61–130286 A, Miyano Seiji, Jun. 18, 1986.

March, J., "Advanced Organic Chemistry", 4th Ed., p. 920, 1992.

*Primary Examiner*—Joseph K. McKane
*Assistant Examiner*—Joseph Murray
*Attorney, Agent, or Firm*—Evenson, McKeown, Edwards & Leahan, P.L.L.C.

[57] ABSTRACT

This invention relates to substituted heterocyclic benzocycloalkenes of general formula I

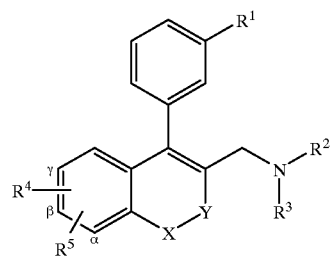

or pharmaceutically acceptable salts thereof, to a method of producing them and to their use as analgesics.

12 Claims, No Drawings

SUBSTITUTED HETEROCYCLIC BENZOCYCLOALKENES AND THE USE THEREOF AS SUBSTANCES HAVING AN ANALGESIC EFFECT

This invention relates to substituted heterocyclic benzocycloalkenes of general formula I

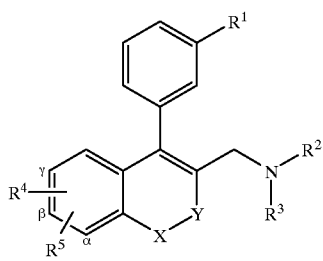

wherein $R^1$ denotes OH, $C_{1-6}$-alkoxy or —O—$(C_{3-7})$-cycloalkyl;

$R^2$ denotes $C_{1-6}$-alkyl;

$R^3$ denotes $C_{1-6}$-alkyl, —$(CH_2)_{1-2}$-aryl, —$(CH_2)_{1-2}$-heterocyclyl, —$CH_2$—$CH$=$C(R^6)_2$, or —$CH_2$—$(C_{3-7})$-cycloalkyl;

$R^4$ and $R^5$, identically to or differently from each other, denote H, Cl, F, $CF_3$, $C_{1-6}$-alkyl, OH, $C_{1-6}$-alkoxy, O—$(C_{3-7})$-cycloalkyl, —$(CH_2)_{0-2}$-aryl, —O—$(CH_2)_{0-2}$-aryl, $\alpha,\beta$- or $\beta,\gamma$-O—$(CH_2)_{1-2}$—O—, heterocyclyl, $\alpha,\beta$- or $\beta,\gamma$-benzo which are unsubstituted, mono- or disubstituted with Cl, F, $CF_3$, OH, $C_{1-6}$ alkyl or $C_{1-6}$-alkoxy, or —$CON(R^6R^7)$;

$R^6$ denotes H or $C_1$–$C_6$-alkyl;

$R^7$ denotes H, $C_1$–$C_6$-alkyl, —$(CH_2)_{0-2}$-aryl or —$CH_2$—$(C_3$–$C_7)$-cycloalkyl, or $R^6$ and $R^7$ taken together denote (—$CH_2$—$)_{5-7}$ or (—$CH_2)_2$—O—$(CH_2)_2$—, X denotes O, S, SO or $SO_2$, and Y denotes —$(CH_2)_{1-2}$—, —$CH_2$—$C(CH_3)_2$— or —$C(CH_3)_2$—, or pharmaceutically acceptable salts thereof. The invention also relates to a method for the production thereof, and to the use thereof as a drug.

Classical opioids such as morphine are very effective for the therapy of severe and very severe pain. Their use is limited, however, by the occurrence of their known side effects, such as respiratory depression, vomiting, sedation and obstipation, and by the development of tolerance. Moreover, they are less effective for neuropathic or incidental pain, such as that from which cancer patients suffer in particular.

Opioids develop their analgesic effect by binding to receptors which are situated on membranes and which form part of the family of what are termed G protein-coupled receptors. The biochemical and pharmacological characterisation of subtypes of these receptors has now given rise to the hope that subtype-specific opioids may exhibit a different profile of effects and side effects to that of morphine, for example. Whereas morphine binds selectively to what are terined, $\mu$-receptors, endogenous enkephalins have been characterised as $\delta$ selective peptides. In the meantime, further pharmacological investigations have indicated that it is probable that there is a plurality of subtypes of these opioid receptors which exist ($\mu_1$, $\mu_2$, $\kappa_1$, $\kappa_2$, $\kappa_3$, $\delta_1$ and $\delta_2$).

Knowledge of the physiological significance of $\delta$-receptor-selective substances has essentially been broadened by the discovery of the non-peptidic antagonist inaltrindol. Thus it has been determined in the meantime that $\delta$-agonists possess an autonomous antinociceptive potential. In addition to a multiplicity of experiments on animals, an investigation has also been performed using the peptidic agonist D-alanine$^2$-D-leucine$^5$enkeplialin (DADL) on cancer patients on whom morphine no longer had an analgesic effect. When administered intrathecally, DADL exhibited a long-lasting analgesic effect.

There is a significant difference between $\delta$- and $\mu$-agonists as regards their interaction with the "endogenous opioid antagonist" cholecystokinin (CCK).

Apart from this different effect profile, the side-effect profile of $\delta$-agonists can also differ from that of $\mu$-agonists, e.g. by a lower extent of respiratory depression. These compounds are of potential use therapeutically as analgesics or, in a quite general manner, are of potential use for all pathological conditions which are usually treated with $\delta$-opiate receptors.

The underlying object of the present invention is therefore to identify substances having an analgesic effect, the biological efficacy of which is brought about, predoominantly or in part, via $\delta$-opiatc receptors.

These requirements have been fulfilled by the substituted heterocyclic benzocyclalkene compounds of the present invention.

The present invention relates to substituted heterocyclic benzocycloalkenes of general formula I

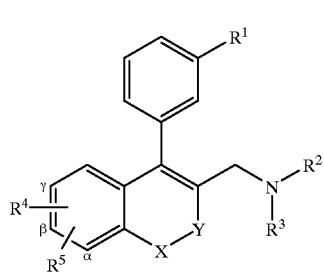

wherein $R^1$ denotes OH, $C_{1-6}$-alkoxy or —O—$(C_{3-7})$-cycloalkyl;

$R^2$ denotes $C_{1-6}$-alkyl, $R^3$ denotes $C_{1-6}$-alkyl, —$(CH_2)_{1-2}$-aryl, —$(CH_2)_{1-2}$-heterocyclyl, —$CH_2$—$CH$=$C(R^6)_2$, or —$CH_2$—$(C_{3-7})$-cycloalkyl;

$R^4$ and $R^5$, identically to or differently from each other, denote H, Cl, F, $CF_3$, $C_{1-6}$-alkyl, OH, $C_{1-6}$-alkoxy, O—$(C_{3-7})$-cycloalkyl, —$(CH_2)_{0-2}$-aryl, —O—$(CH_2)_{0-2}$-aryl, $\alpha,\beta$- or $\beta,\gamma$-O—$(CH_2)_{1-2}$—O—, heterocyclyl, $\alpha.\beta$- or $\beta,\gamma$-benzo which are unsubstituted, mono- or disubstituted wvith Cl, F, $CF_3$, OH, $C_{1-6}$-alkyl or $C_{1-6}$-alkoxy, or —$CON(R^6R^7)$;

$R^6$ denotes H or $C_1$–$C_6$-alkyl, $R^7$ denotes H, $C_1$–$C_6$-alkyl, —$(CH_2)_{0-2}$-aryl or —$CH_2$—$(C_3$–$C_7)$-cycloalkyl, or $R^6$ and $R^7$ taken together denote (—$CH_2$—$)_{5-7}$ or (—$CH_2)_2$—O—$(CH_2)_2$—, X denotes O, S, SO or $SO_2$, and Y denotes —$(CH_2)_{1-2}$—, —$CH_2$—$C(CH_3)_2$— or —$C(CH_3)_2$—, or pharmaceutically acceptable salts thereof.

The preferred compounds of general formula I are those in which X denotes O, S or SO, Y denotes —$(CH_2)_{1-2}$ and $R^1$ to $R^7$ have the meaning according to the definition of general formula I, or X denotes O, Y denotes —$(CH_2)_{1-2}$— and $R^1$ to $R^7$ have the meaning according to the definition of general formula I, or $R^4$ and $R^5$, identically to or independently of each other, denote —O—$(CH_2)_{0-2}$-aryl, —$(CH_2)_{0-2}$-aryl or heterocyclyl and $R^1$ to $R^3$, $R^6$, $R^7$, X and Y have the meaning as defined above, or $R^1$ denotes $C_{1-6}$-alkoxy or O—$(C_{3-7})$-cycloalkyl. $R^4$ and $R^5$, identically to or differently from each other, denote —$(CH_2)_{0-2}$ aryl or heterocyclyl, and $R^2$, $R^3$, $R^6$, $R^7$, X and Y have the meaning as defined above, or $R^1$ denotes OH or $C_{1-6}$-alkoxy and $R^2$ to $R^7$, X and Y have the meaning as defined in detail above, or Y denotes —$(CH_2)_{1-2}$—, $R^2$ denotes $C_{1-6}$-alkyl, and X, $R^1$ and $R^3$ to $R^7$ have the meaning according to the definition of general formula I, or Y denotes —$(CH_2)_{1-2}$—, $R^1$ denotes OH or $C_{1-6}$-alkoxy, $R^2$ and $R^3$ denote $C_{1-6}$-alkyl, and X and $R^4$ to $R^7$ have the meaning according to the definition of general formula I, or Y denotes —$(CH_2)_{1-2}$—, $R^1$ denotes OH, $R^2$ and $R^3$ denote $C_{1-6}$-alkyl, X denotes O and $R^4$ to $R^7$ have the meaning according to the definition of general formula I.

In the present invention, the expression "$C_{1-6}$-alkyl" means straight chain or branched hydrocarbon radicals comprising 1–6 carbon atoms. Examples thereof include methyl, ethyl, propyl, isopropyl, n-butyl, sec-butyl, tert-butyl, n-pentyl, neopentyl and n-hexyl.

In the context of the present invention, the expression "$C_{1-6}$-alkoxy" means straight chain or branched hydrocarbon radicals comprising 1–6 carbon atoms as defined above which are bonded via an oxygen atom.

In the context of the present invention, the "aryl" means phenyl groups which are unsubstituted or which are singly- or multiply-substituted with OH, F, Cl, $CF_3$, $C_{1-6}$-alkyl, $C_{1-6}$-alkoxy, $C_{3-7}$-cycloalkyl, $C_{2-6}$-alkylene, heterocyclyl or phenyl groups. The expression may also optionally mean naphthyl.

In the context of the present invention, the expression "heterocyclyl" is to be understood to mean radicals derived from 5- or 6-membered, saturated or unsaturated heterocyclic compounds, which are optionally provided with an aryl system which is condensed thereon, and which contain 1 or 2 hetero atoms from the group comprising nitrogen, oxygen and/or sulphur.

Examples of compounds from which saturated heterocyclyl radicals are derived include 1,4-dioxane, tetrahydrofuran, 1,2-oxathiolane, pyrrolidine and piperazine.

In the context of the present invention, examples of the group comprising unsaturated heterocyclyl radicals e comprise those derived from thiophen, pyrrole, pyridine, pyrimidine, 1,3-thiazole, oxazole, isoxazole, imidazole, pyrazole, γ-pyrane, γ-thiapyrane, pyradizine, pyrazine, 1,4-thiazine, quinoline, isoquinoline and quinazoline.

In the context of the present invention, the expression "silanyl compound" is to be understood to mean those from which trialkyl, triarylsilyl or diarylalkylsilyl radicals are derived which are used as a protective group for the hydroxy function. Examples include triethylsilyl, tripropylsilyl, dimethyl-phenylsilyl, di-tert-butylphenylsilyl, triisopropylsilyl, dimethylisopropylsilyl, diethylisopropylsilyl, dimethylhexyl-silyl, tert-butyldimethylsilyl, tert-butyldiphenylsilyl, tribenzylsilyl, tri-p-xylylsilyl, triphenylsilyl, diphenyl-methylsilyl or propyl-diphenylsilyl radicals.

The present invention also relates to a method of producing substituted heterocyclic benzocycloalkenes of general formula (I), which is characterised by the reaction of a tertiary alcohol of general formula II.

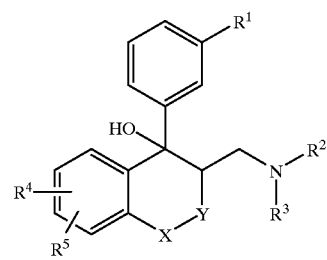

II wherein $R^1$ to $R^7$, X and Y have the same meaning as in formula I, with semiconcentrated or concentrated organic or inorganic acids, most preferably formic acid or hydrochloric acid, at temperatures betnween 0° C. and 100° C., preferably +50° C., wherein the tertiary alchlols of general formula II are obtained by the reaction of Mannich bases of general formula III

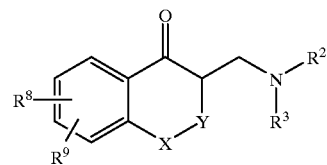

III wherein $R^2$, $R^3$, X and Y have the same meaning as in formula I, $R^8$ is defined as is $R^4$, and $R^9$ is defined as is $R^5$, with the exception that any hydroxy function which is exists is present in protected form as a benzyloxy or silanyloxy group, with an organometallic compound of formula IV

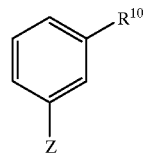

IV wherein Z represents MgCl, MgBr, MgI or Li, and $R^{10}$ has the meaning according to $R^1$, with the exception that any hydroxy function which is exists is present in protected form as a benzyloxy or silanyloxy group, e.g. as tert-butyldiphenylsilyloxy, which are reacted to form a compound of formula IIa

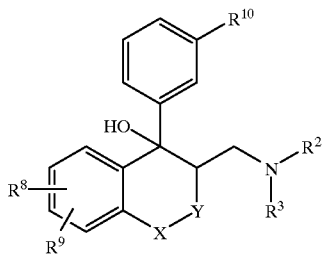

IIa and the latter are then converted into compounds of formula II.

The reaction of compounds III and IV is conducted in an aliphatic ether, for example diethyl ether and/or tetrahydrofuran, at temperatures between −70° C. and +60° C. Compounds of formula IV, in which Z represents a lithium atom, can be obtained from compounds of formula IV, in which Z denotes Br or I, by halogen-lithium exchange by means of a solution of n-butyllithium in n-hexane, for example.

There is a plurality of methods which are available for the reaction of a compound of formula IIa to form a compound of formula II, depending on $R^8$, $R^9$ or $R^{10}$.

If $R^8$, $R^9$ and/or $R^{10}$ represent a benzyloxy group, the reaction is advantageously effected by reductive debenzylation with catalytically activated hydrogen, wherein platinum or palladium, absorbed on a support material such as activated carbon, is employed as the catalyst. The reaction is conducted in a solvent such as acetic acid or a $C_{1-4}$-alkyl alcohol at pressures of 1 to 100 bar and temperatures of +20° C. to +100° C., wherein compound IIa is preferably used in the form of one of its salts.

If $R^9$ and/or $R^{10}$ represent a silanyloxy group, separation of the protective group is effected by reacting the corresponding compound or formula IIa with tetra-n-butylammonium fluoride at −20° C. in an inert solvent such as tetrahydrofuran, dioxane or diethyl ether, or by treating it with a methanolic solution of hydrogen chloride.

If $R^8$, $R^9$ and/or $R^{10}$ in the compound of formula IIa represent a methoxy radical, the compound of formula II, in which $R^1$ represents a hydroxy group, can be produced by reaction with diisobutylaluminium hydride in an aromatic hydrocarbon such as toluene at a temperature between 60° C. and 130° C. The analogous compound of formula I can also be obtained directly by heating IIa, under reflux, either with a solution of hydrogen bromide in glacial acetic acid or with concentrated hydrobromic acid.

Compounds of formula I in which $R^1$ and/or $R^4$ or $R^5$ represent a methoxy group can also be obtained as described above by reaction with diisobutylaluminium hydride compounds of formula I in which $R^1$ and/or $R^2$ or $R^5$ similarly contain OH. This is also possible by reaction with methanesulphonic acid/methionine at temperatures between 20° C. and 50° C.

Compounds of formula I, in which X denotes an SO or $SO_2$ group, can be produced from compounds of formula I, in which X represents an S atom, by oxidation with hydrogen peroxide (30% by weight in water) and in acetic acid as a solvent at temperatures between +20° C. and +60° C.

The compounds of formula I can be converted into their salts in the known manner with physiologically compatible acids such as hydrochloric acid, hydrobromic acid, sulphuric acid, methanesulphonic acid, formic acid, acetic acid, oxalic acid, succinic acid, tartaric acid, mandelic acid, fumaric acid, lactic acid, citric acid, glutamic acid and/or aspartic acid. Salt formation is preferably conducted in a solvent such as diethlyl ether, diisopropyl ether, an alkyl ester of acetic acid, acetone and/or 2-butanone. Trimethlylchlorosilane in aqueous solution is particularly suitable for the production of hydrochlorides.

EXAMPLES

The following examples serve to provide a more detailed explanation of the present invention.

Silica gel 60 (0.040–0.063 mm) supplied by E. Merck, Darmstadt, was used as the stationary phase for column chromatography.

Thin-layer chromatography investigations were performed using ready-made plates of silica gel 60 F 254 supplied by E. Merck, Darmsstadt.

The mixture ratios of the mobile phases for all the chromatographic investigations are always given in volunme/volume.

The expression Tris-HCl means tris-(hydroxymethyl)-aminomethane hydrochloride.

(w/v)=weight/volume

Example 1

3-(4-dimethylaminomethyl-2,3-dihydro-benzo[b] thiepin-5-yl)-phenol hydrochloride 1st Step (RS)-4-dimethylaminomethyl-3,4-dihydro-2H-benzo[b] thiepin-5-one hydrochloride A solution of 32.1 g 3,4-dihydro-2H-benzo[b]thiepin-5-one in 320 ml acetonitrile was treated with 16.9 g N,N-dimethylmethyleneimmonium chloride and with three drops of acetyl chloride, and the mixture was stirred for 72 hours at 20° C. The batch was then diluted with 100 ml diethyl ether, and the crystalline product was isolated, washed with diethyl ether and dried under vacuum at 40° C. 44.1 g (90.0 % theoretical) of the title compound were thus obtained in the form of white crystals.

Melting point: 183–185° C.

2nd Step:

(4RS, 5RS)-5-[3-tert-butyl-diphenyl-silaniyloxy)-phenyl]-4-dimethylaminomethyl-2,3,4,5-tetrahydro-benzo[b] thiepin-5-ol A solution of 32.9 g (3-bromophenoxy)-tert-butyl-diphenyl-silane in 250 ml of dry tetrahydrofuran was treated drop-wise, at −40° C. with stirring and whilst passing dry nitrogen over the batch, with 50 ml of a 1.6 molar solution of n-butyllithium in n-hexane. After the addition was complete, the batch was stirred for a further 30 minutes at −40° C. to −30° C., and a solution of 15.1 g of the free base of the product from step 1 in 40 ml of dry tetrahydrofuran was then added drop-wise thereto. The batch was stirred for a further 4 hours at this temperature, and was then decomposed by the addition of 50 ml of a saturated ammonium chloride solution. The organic phase was separated, and the aqueous phase was extracted twice with ethyl acetate. The combined organic phases were washed with a saturated sodium chloride solution and dried over sodium sulphate. After filtration and evaporation of the solvent under vacuum, 11.4 g (31.3% theoretical) of the title compound remained in the form of a colourless viscous oil.

3rd Step:

(4RS, 5RS)-4-dimethylaminomethyl-5-(3-hydroxy-phenyl)-2,3,4,5-tetrahydrobenzo[b]thiepin-5-ol A solution of 11.4 g of the product from step 2 in 200 ml dry tetrahydrofuran was treated drop-wise at 5° C., with stirring, with 22 ml of a 1 M solution of tetra-n-butylimmonium fluoride in tetrahydrofuran. After the addition was complete, the batch was stirred for 3 hours at 20° C., was treated with 50 ml of a saturated solution of ammonium chloride, and was extracted three times with 50 ml ethyl acetate each time. The extracts were washed with saturated sodium chloride solution, dried over sodium sulphate and concentrated by evaporation under vacuum. The residue was purified by column chromatography using ethyl acetate/methanol (9/1) as the elutant. 6 g (90.8% theoretical) of the title compound were thus obtained in the form of white crystals, which melted at 188–190° C.

4th step:
3-(4-dimethylaminomethyl-(2,3-dihydro-benzo[b]thiepin-5-yl)-phenol hydrochloride A solution of 4.95 g of the compound from step 3 in 50 ml tetrahydrofuran was treated with 150 ml 6N hydrochloric acid and the mixture was stirred for 48 hours at 20° C. and then for 24 hours at 60° C. The batch was made alkaline with aqueous sodium hydroxide solution and was extracted three times with 100 ml ethyl acetate each time. The extracts were washed with saturated sodium chloride solution, dried over sodium sulphate and concentrated by evaporation under vacuum. There remained 4.44 g (95.0% theoretical) of the free base of the title compound as a white solid (melting point: 217–219° C.), which was converted into the hydrochloride with trimethylchlorosilane/water in a solvent mixture comprising 2-butanone and tetrahydrofuran (1/2).
Melting point: 251–253° C.

Example 2

The following substances were obtained similarly, using the procedure described in Example 1 but using corresponding cyclic ketones instead of 3,4-dihydro-2H-benzo[b]thiepin-5-one in step) 1:

2a: 3-(8-chloro-3-dimethylaminomethyl-2H-chromen-4-yl)-phenol hydrochloride

2b: 3-(3-dimethylaminomethyl-2H-benzo[b]chromen-4-yl-phenol hydrochloride
Melting point: 232–235° C.

2c: 3-(2-dimethylaminomethyl-3H-4-thiaphenanthren-1-yl)-phenol hydrochloride
Melting point: 246–248.5° C.

2d: 3-(7-dimethylaminomethyl-2,3-dihydro-6H-1,4,5,-trioxa-phenanthren-8-yl)-phenol hydrochloride
Melting point: 229–231° C.

2e: 3-(4-dimethylaminomethyl-2,3-dihydro-benzo[b]oxepin-5-yl)-phenol hydrochloride
Melting point: 235–237° C.

2f: 3-(3-dimethylaminomethyl-6)-methoxy-2,2-dimethyl-2H-chromen-4-yl)-phenol hydrochloride
Melting point: 217–219° C.

2g: 3-(4-dimethylaminomethyl-8-methoxy-2,3-dihydrobenzo[b]oxepin-5-yl)-phenol hydrochloride
Melting point: 206–208° C.

2h: 3-(4-dimethylaminomethyl-8-methoxy-2,3-dihydrobenzo[b]thiepin-5-yl)-phenol hydrochloride
Melting point: 232–235° C.

2i: 3-(4-dimethylaminomethyl-8-fluoro-2,3-dihydrobenzo[b]thiepin-5-yl)-phenol hydrochloride
Melting point: decomposition above 130° C.

2j: 3-(4-dimethylaminomethyl-8-fluoro-2,3-dihydrobenzo[b]oxepin-5-yl)-phenol hydrochloride
Melting point: 245–247° C.

2k: 3-(7-tert-butyl-4-dimethylaminomethyl-2,3-dihydrobenzo[b]oxepin-5-yl)-phenol hydrochloride
Melting point: 264–266° C.

2l: 3-(7,8-dichloro-4-dimethylaminomethyl-2,3-dihydro-benzo[b]oxepin-5-yl)-phenol hydrochloride
Melting point: 219–220° C.

2m: 3-(4-dimethylaminomethyl-9-methoxy-2,3-dihydro-benzo[b]oxepin-5-yl)-phenol hydrochloride
Melting point: 194–196 ° C.

2n: 3-(8-benzyloxy-4-dimethylaminomethyl-2,3-dihydro-benzo[b]oxepin-5-yl)-phenol hydrochloride
Melting point: 234–236 ° C.

Example 3

3-(4-dimethylaminomethyl-1-oxo-2,3-dihydro-1H-1$\lambda^4$-benzo[b]thiepin-5-yl)-phenol hydrochloride (racemate and enantiomers)

A mixture of 1.74 g of the product from Example 1, 17 ml glacial acetic acid and 1.6 ml of an aqueous solution of hydrogen peroxide (30% by weight $H_2O_2$) was stirred for 2 hours at 20° C. Thereafter the batch was diluted with 50 ml water and was made alkaline with aqueous sodium hydroxide to a pH of 9. The batch was extracted three times with 30 ml ethyl acetate each time. The combined extracts were washed with saturated sodium chloride solution, dried over sodium sulphate and concentrated by evaporation under vacuum. The residue was converted into the hydrochloride as described in Example 1, step 4. 1.68 g (92.4% theoretical) of the racemic title compound was thus obtained in the form of white crystals, which melted at 208–210° C. The enantiomers were obtained in pure form by HPLC on a stationary phase, using n-hexane/isopropanol/diethylamine (950/50/1).

Example 4

3-(4-dimethylaminomethyl-1,1-dioxo-2,3-dihydro-1H-1$\lambda^6$-benzo[b]thiepin-5-yl)-phenol hydrochloride 0.91 g of the product from Example 3 in 4.5 ml glacial acetic acid were stirred for 24 hours at 45° C. with 0.5 ml of an aqueous solution of hydrogen peroxide (30% by weight $H_2O_2$). After work-up as described in Example 2, purification of the crude product by column chromatography using ethyl acetate/methanol (5/1) as the elutant, and conversion of the purified substance into the hydrochloride, 0.67 g (70.3% theoretical) of the title compound were obtained in the form of white crystals which melted at 263–266° C.

Example 5

3-(3-dimethylaminomethyl-2H-thiochromen-4-yl)-phenol hydrochloride

1st step:
(3RS, 4RS)-3-dimethylaminomethyl-4-(3-methoxy-phenyl)-thiochroman-4-ol The corresponding Grignard reagent was prepared from 0.73 g magnesium turnings and 5.61 g 1-bromo-3-methoxybenzene in 20 ml of dry tetrahydrofuran, with gentle boiling. A solution of 4.43 g (RS)-3-dimethylaminomethyl-thiochroman-4-one in 10 ml dry tetrahydrofuran was added drop-wise thereto at +5 to 10° C. The batch was subsequently stirred for 6 hours at 20° C. and was then decomposed with 10 ml of a saturated ammonium chloride solution. The batch was extracted three times with diethyl ether, and the combined extracts were washed with a saturated sodium chloride solution and dried over sodium sulphate. The crude product which remained after evaporating off the volatile constituents was purified by column chromatography using ethyl acetate as the elutant, whereupon 3.68 g (55.8% theoretical) of the title compound was obtained.

2nd step:
3-(3-dimethylaminomethyl-2H-thiochromen-4-yl)-phenol hydrochloride 3.3 g of the product from step 1 were stirred for 8 hours at 100° C. to 110° C. with 90 ml of a solution of hydrogen bromide in glacial acetic acid (33% HBr). The batch was then concentrated by evaporation under vacuum and the residue was taken up in 100 ml water. It was made alkaline with sodium carbonate and extracted three times with 30 ml dichloromethane each time. The extracts were dried over sodium sulphate and concentrated by evaporation, and the residue was purified by column chromatography using ethyl acetate as the elutant. The base of the title compound which was thus obtained was converted into the hydrochloride with trimethylchlorosilane/water in 2-butanone.

Yield: 1.40 g (41.7% theoretical) Melting point: 203–208° C.

Example 6

[4-(3-methoxy-phenyl)-2H-chromen-3-ylmethyl]-dimethylamine

1st step:
(3RS, 4RS)-3-dimethylaminomethyl-4-3-methoxy-phenyl)-chroman-4-ol 3.91 g (62.4% theoretical) of the title compound was obtained by the procedure as in Example 5, step 1, comprising the reaction of 4.11 g (RS)-3-dimethylaminomethyl-chroman-4-one with the Grignard reagent formed from 0.73 g magnesium turnings and 5.61 g 1-bromo-3-methoxybenzene, and analogous purification.

2nd step:
[4-(3-methoxy-phenyl)-2H-chromen-3-ylmethyl]-dimethylamine

A solution of 3.9 g of the product from step 1 in 20 ml ethanol was reacted as described in Example 1, step 4, with 14.5 ml 6N hydrochloric acid for 2 hours at 20° C. After an analogous work-up stage and purification by column chromatography using ethyl acetate as the elulant, 2.1 g (57.1% theoretical) of the title compound were obtained as an almost colourless oil which solidified at 4° C. (melting point: 68–71° C.).

Example 7

3-(3-dimethylaminomethyl-2H-chromen-4-yl)-phenol hydrochloride

A solution of 0.59 g of the product from Example 6 in 10 ml methanesulphonic acid was treated under an $N_2$ atmosphere with 0.59 g methionine, whereupon a brown solution was formed. This was stirred for one hour at 20° C. and was then shaken on to iced water. 50 ml ethyl acetate were added thereto, and the mixture was made alkaline with aqueous sodium carbonate solution. The organic phase was separated, and the aqueous phase was extracted twice with 20 ml ethyl acetate each time. The organic phases were washed with saturated sodium chloride solution, dried over sodium sulphate and freed from the volatile constituents under vacuum. The residue was purified by column chromatography using ethyl acetate/methanol (5/1). The product which was thus obtained was converted into the hydrochloride as described in Example 1, step 4.

Yield: 0.26 g (48.1% theoretical) Melting point: 213–215° C.

Example 8

3-dimethylaminomethyl-4-(3-hydroxy-phenyl)-2,2-di-methyl-2H-chromen-6-ol hydrochloride 1st step:
(3RS,4RS)-6-benzyloxy-3-dimethylaminomethyl-4-(3-hydroxy-phenyl)-2,2-dimethyl-chroman-4-ol hydrochloride The free base of the title compound, which was subsequently converted into the hydrochloride as described in Example 1, step 4, was obtained by employing the reaction sequence described in Example 1, steps 1–3, and the reagents used there, except that 6-benzyloxy-2,2-dimethylchroman-4-one was used instead of 3,4-dihydro-2H-benzo[b]thiepin-5-one.

Melting point: 142–143° C.

2nd step:
(3RS, 4RS)-3-dimethylaminomethyl-4-(3-hydroxy-phenyl)-2,2-dimethyl-chroman-4,6-diol hydrochloride 1.08 g of the product from step 1, dissolved in 15 ml of anhydrous methanol, were catalytically hydrogenated over 0.11 g palladium on activated carbon (10% Pd). After filtering off the catalyst and evaporating the solvent under vacuum, 0.83 g of the title compound remained, which was sufficient for further reaction.

3rd step:
3-dimethylaminomethyl-4-(3-hydroxy-phenyl)-2,2-di-methyl-2H-chromen-6-ol hydrochloride 0.83 g of the product from step 2 were treated with 20 ml 6N hydrochloric acid and the resulting solution was stirred for 2 hours at 20° C. The batch was then made alkaline with dilute aqueous sodium hydroxide (pH 8–9) and was extracted three times with 20 ml dichloromethane each time. The combined extracts were dried over sodium sulphate and were concentrated by evaporation under vacuum. The residue was purified by column chromatography using ethyl acetate/methaniol (5/1) as the elutant. After converting the product into the hydrochloride with chlorotrimethylsilane/water in 2-butanone, 0.57 g (72.2% theoretical) of the title compound was obtained in the form of white crystals which melted at 195–198° C.

Example 9

The following substances were obtained similarly, by employing the procedure described in Example 3 and using the products from Examples 2h and 2i instead of the product from Example 1:

9a: 3-(4-dimethylaminomethyl-8-methoxy-1-oxo-2,3-dihydro-1H-1-2-4-benzo[b]thiepin-5-yl)-phenol hydrochloride Melting point: from 222° C. with decomposition 9b: 3-(4-dimethylaminomethyl-8-fluoro-1-oxo-2,3-dihydro-1H-1λ4-benzo[b]thiepin-5-yl)-phenol hydrochloride Melting point: from 198° C. with decomposition

Example 10

The following substance was obtained similarly, by employing the procedure described in Example 4 and using the product from Example 9a instead of the product from Example 3:

3-(4-dimethylaminomethyl-8-methoxy-1,1-dioxo-2,3-dihydro-1H-1λ6-benzo[b]thiepin-5-yl)-phenol hydrochloride Melting point: 253–256° C.

Example 11

The following substances were obtained similarly, by employing the procedure described in Example 7 and using the products from Examples 2g or 2h instead of the product from Example 6:
11a: 4-dimethylaminomethyl-5-(3-hydroxy-phenyl)-2,3-dihydro-benzo[b]oxepin-8-ol hydrochloride
Melting point: from 103° C. with decomposition
11b: 4-dimethylaminomethyl-5-(3-hydroxy-phenyl)-2,3-dihydro-benzo[b]thiepin-8-ol hydrochloride
Melting point: from 117 ° C. with decomposition Example 12

4-dimethylaminomethyl-5-(3-hydroxy-phenyl)-2,3-dihydro-benzo[b]oxepin-7-carboxylic acid-diethylamide hydrochloride 1st step:
7-bromo-3,4-dihydro-2H-benzo[b]oxepin-5-one, as the ethylene acetal A mixture of 24.1 g 7-bromo-3,4-dihydro-2H-benzo[b]oxepin-5-one, 8.5 ml ethylene glycol and 0.35 g p-toluenesulphonic acid monohydrate was heated under reflux for 24 hours in an apparatus fitted with a water separator trap. After the water of reaction had been separated, 4 g powdered potassium carbonate was added to the reaction mixture and the batch was stirred for one hour at 20° C. Thereafter, the salt was filtered off and the filtrate was concentrated by evaporation under vacuum. 27 g of the title compound remained as a brown oil.

2nd step:
5-oxo-2,3,4,5-tetrahydro-benzo[b]oxepin-7-carboxylic acid, as the ethylene acetal A solution of 27 g of the product from step 1 in 280 ml of anhydrous tetrahydrofuran was treated drop-wise with 62 ml of a 1.6 molar solution of n-butyllithium in n-hexane at −50° C., whilst stirring and passing nitrogen over the batch. After the addition was complete, the batch was stirred for a further 30 minutes, and then carbon dioxide was passed into the solution at −40 to −50° C. until saturation was achieved. The batch was allowed to warm up to 20° C. over 3 hours, was decomposed by the addition or 50 ml of a saturated ammonium chloride solution, the organic phase was separated, and the aqueous phase was extracted twice with 50 ml ethyl acetate each time. The combined organic phases were washed with a saturated sodium chloride solution and dried over sodium sulphate. The residue which was obtained by evaporation under vacuum was purified by column chromatography using ethyl acetate as the elutant. 16.4 g (69.1% theoretical) of the title compound was thus obtained in the form of an oil.

3rd step:
5-oxo-2,3,4,5-tetrahydro-benzo[b]oxepin-7-carboxylic acid-diethylamide, as the ethylene acetal A solution of 16.1 g of the product from step 2 in 40 ml cyclohexane and 25 ml thionyl chloride was stirred for 2 hours at 20° C. under an $N_2$ atmosphere. The volatile constituents were then carefully evaporated under vacuum. The crude carboxylic acid chloride which remained behind was dissolved in 70 ml tetrahydrofuran and the solution was added drop-wise, whilst stirring and cooling in iced water, to a solution of 8.7 ml diethylamine in 150 ml tetrahydrofuran. Thereafter, the batch was stirred for a further 2 hours at 20° C. The solids were filtered off under suction and were thoroughly washed with tetrahydrofuran, and the filtrate was concentrated by evaporation under vacuum. The residue was purified by column chromatography using ethyl acetate/n-hexane (3/1) as the elutant, whereupon 8.9 g (45.5% theoretical) of the title compound was obtained as an oil.

4th step:
5-oxo-2,3,4,5-tetrahydro-benzo[b]oxepine-7-carboxylic acid-diethylamide A mixture of 8.7 g of the product from step 3, 15 ml tetrahydrofuran and 30 ml 1N hydrochloric acid was stirred for 20 hours at 20° C. The batch was then extracted three times with ethyl acetate. The extracts were washed with a saturated sodium chloride solution, were dried over sodium sulphate and were concentrated by evaporation under vacuum. 7.37 g (98.9% theoretical) of the title compound remained behind a slightly yellow, viscous oil 5th step:
(RS)-4-dimethylaminomethyl-5-oxo-2,3,4,5-tetrahydro-benzo[b]oxepinc-7-carboxylic acid-diethylamide hydrochloride 7.2 g of the prodluct from step 4 were reacted as described in Example 1, step 1, with 2.7 g N,N-dimethylmethyleneimmonium chloride. 8.8 g (90.1%, theoretical) of the title compound were thus obtained in the form of white crystals, which melted at 178–180° C.

6th step:
(4RS,5RS)-5-[3-(tert-butyl-dimethyl)-silanyloxy)-phenyl]-4-dimethylaminomethyl-5-hydroxy-2,3,4,5-tetrahydro-benzo[b]oxepine-7-carboxylic acid-diethylainide 9.5 g (3-bromophenoxy)-tert-butyl-diphenyl-silane, 20.2 ml of a 1.6 molar solution of n-butyllithium in n-hexane and 7.8 g of the product from step 5, as the free base, were reacted by the procedure described in Example 1, step 2. After work-up and purification by column chromatography using ethyl acetate/methanol (5/1), 8.29 g (64.3% theoretical) of the title compound were obtained as a slightly yellow oil.

7th step:
(4RS,5RS)-4-dimethylaminomethyl-5-hydroxy-5-(3-hydroxy-phenyl)-2,3,4,5-tetrahydro-benzo[b]oxepine-7-carboxylic acid-diethylamide 8.2 g of the product from step 6 and 50 ml 6N hydrochloric acid were stirred for 48 hours at 20° C. After making the batch alkaline with aqueous sodium hydroxide, it was extracted three times with 30 ml ethyl acetate each time. The extracts were washed with saturated sodium chloride, dried over sodium sulphate and concentrated by evaporation under vacuum. Purification of the residue by column chromatography using ethyl acetate/methanol (3/1) as the elutant gave 5.32 g (82.8% theoretical) of the title compound.

8th step:
4-dimethylaminomethyl-5-(3-hydroxy-phenyl)-2,3-dihydrobenzo[b]oxepine-7-carboxylic acid-diethylamide hydrochloride 5.6 g of the product from step 7, in the form of the hydrochloride, were heated with 70 ml formic acid at a bath temperature of 110° C. with stirring for 2 hours. After cooling, the batch was made alkaline with aqueous sodium hydroxide and potassium carbonate (pH 9) and was extracted three times with dichloromethane. The extracts were washed with saturated sodium chloride solution, dried over sodium sulphate and concentrated by evaporation under vacuum. The hydrochloride was prepared from the residue by treating it with trimethylchlorosilane/water in 2-butanone. 4.91 g (91.3% theoretical) of the title compound were thus obtained in the form of white crystals, which melted from 234° C. with decomposition.

Example 13

3-{4-[(methyl-phenethyl-amino)-methyl]-2,3-dihydro-benzo[b]oxepin-5-yl}-phenol hydrochloride 1st step:
(RS)-4-[(methyl-phenethyl-amino)-methyl]-3,4-dihydro-2H-benzo[b]oxepin-5-one A mixture of 24.4 g 3,4-dlihydro-2H-benzo[b]oxepin-5-one, 17.2 g N-methyl-2-phenylethylamine hydrochloride and 3.0 g paraformaldehyde in 200 ml glacial acetic acid was heated at 100° C. for 3 hours. Thereafter, the solvent was evaporated under vacuum and the residue was taken up in 200 ml water. The product was extracted three times with 100 ml diethyl ether each time. The aqueous phase was made alkaline with potassium carbonate and was extracted three times with 100 ml dichloromethane each time. After washing the extracts with saturated sodium chloride solution, drying them over sodium sulphate and concentrating them by evaporation under vacuum, 23.9 g (77.2% theoretical) of the title compound remained behind as a yellowish oil.

Final step:
3-{4-[(methyl-phenethyl-amino)-methyl]-2,3-dihydro-benzo[b]oxepin-5-yl}-phenol hydrochloride The product from step 1 was reacted further by the procedure as described in Example 1, steps 2–4. The title compound was thus obtained in the form of white crystals, which melted from 135° C. with decomposition.

Example 14

3-{4-[(cyclopropyl-methyl-amino)-methyl]-2,3-dihydro-benzo[b]oxepin-5-yl}-phenol hydrochloride Using N-(cyclopropylmethyl)-methylamine hydrochloride as in Example 13, step 1, and with further reaction of the product thus obtained by the procedure as described in Example 1, steps 2–4, the title compound was obtained analogously in the form of white crystals which melted at 216–218° C.

δ-Opiate Receptor Binding Investigations

Investigations for determining the affinity of compounds of formula I according to the invention for the δ-opiate receptor, which is a crucial prerequisite for analgesic properties, were performed on meninge homogenates (rat brain homogenates, without the cerebellum, pons and medulla oblongata, from male Wistar rats). Selected compounds of formula I were used for the detection of δ-opiate receptor properties.

For this purpose, freshly prepared rat brain was homogenised in 50 mmoles/l Tris-HCl (pH 7.4) whilst cooling in ice, and was centrifuged for 10 minutes at 5000 g. After decanting and discarding the supernatant liquor, and renewed take-up and homogenisation of the membrane sediment in 50 mmoles/l Tris-HCl (pH 7.4), the homogenate was subsequently centrifuged for 20 minutes at 20,000 g and 4° C. This washing step was repeated once more. Thereafter, the supernatant liquor was decanted and the membrane sediment was homogenised in cold 50 mmoles/l Tris-HCl, 20% glycerol (w/v), 0.01% bacitracin (w/v) (pH 7.4) and was frozen in aliquots until testing was performed.

For the receptor binding tests, the aliquots were thawed out and diluted 1:10 with the binding test buffer.

The buffer used in the binding test comprised 50 mmoles/l Tris-HCl, 5 mmoles/l MgCl (pH 7.4), supplemented with 0.1% (w/v) bovine serum albumin. 1 mmole/l ($^3$H)-2-D-Ala-deltorphin II was used as the radioactive ligand. The proportion of non-specific binding was determined in the presence of 10 mmoles/l naloxon.

The compounds according to the invention were added to further batches in series of concentrations and the displacement of the radioactive ligand from its specific binding site was determined. The respective triple batches were incubated for 90 minutes at 37° C. and were subsequently harvested by means of filtration through glass fibre filters (GF/B) for the determination of the radioactive ligand bound to the membrane homogenate. The radioactivity of the glass fibre filter discs was measured in a β-counter after adding a scintillator.

The affinity of the compounds according to the invention for the δ-opiate receptor was calculated as the $IC_{50}$ according to the law of mass action by means of nonlinear regression. The K values in Table 1 are given as the mean value±the standard deviation from three mutually independent tests.

TABLE 1

| Example No. | δ-opiate receptor binding $K_i$ [nmoles/l] |
|---|---|
| 1 | 10.2 ± 4.5 |
| 2b | 348 ± 65 |
| 2c | 137 ± 13 |
| 2d | 18.4 ± 1.6 |
| 2e | 8.5 ± 3 |
| 3 | 2.1 ± 0.13 |
| 5 | 68.2 ± 10.1 |
| 7 | 68.4 ± 8.4 |
| 8 | 393 ± 46 |
| 9a | 1,75 ± 0,22 |
| 2g | 6,19 ± 0,31 6.01 |
| 11b | 6,43 ± 0,67 6.71 |
| 2h | 2,67 ± 1,60 1.76 |

What is claimed is:

1. A heterocyclic benzocycloalkene derivative corresponding to formula I:

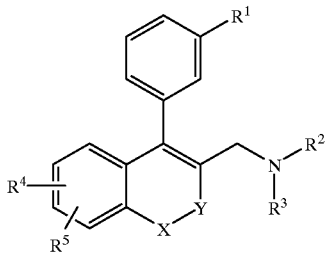

wherein
R$^1$ denotes an OH, C$_{1-6}$-alkoxy or —O—(C$_{3-7}$)-cycloalkyl group;
R$^2$ denotes a C$_{1-6}$-alkyl group;
R$^3$ denotes a C$_{1-6}$-alkyl, —CH$_2$—CH=C(R$^6$)$_2$, or —CH$_2$—(C$_{3-7}$)-cycloalkyl group;
R$^4$ and R$^5$ each independently denotes H, Cl, F, CF$_3$, OH, or a C$_{1-6}$-alkyl, OH, C$_{1-6}$-alkoxy, O—(C$_{3-7}$)-cycloalkyl, —(CH$_2$)$_{0-2}$-aryl, α,β- or β,γ—O—(CH$_2$)$_{1-2}$—O—, —O—(CH$_2$)$_{0-2}$-aryl, heterocyclyl, α,β- or β,γ-benzo group which is unsubstituted or mono- or disubstituted with F, Cl, CF$_3$, OH, C$_{1-6}$-alkyl, C$_{1-6}$-alkoxy, or —CON(R$^6$R$^7$);
R$^6$ denotes H or a C$_{1-6}$-alkyl group;
R$^7$ denotes H, or a C$_{1-6}$-alkyl, —(CH$_2$)$_{0-2}$-aryl, or —CH$_2$—(C$_{3-7}$)-cycloalkyl group; or
R$^6$ and R$^7$ together denote a —(CH$_2$)$_{5-7}$—, or —(CH$_2$)$_2$—O—(CH$_2$)$_2$— group;
X denotes O, S, SO or SO$_2$, and
Y denotes a —(CH$_2$)$_{1-2}$—, —CH$_2$—C(CH$_3$)$_2$—, or —C(CH$_3$)$_2$— group; or a pharmaceutically acceptable salt thereof.

2. A compound according to claim 1, wherein X denotes O, S or SO, and Y denotes a —(CH$_2$)$_{1-2}$— group.

3. A compound according to claim 1, wherein X denotes O, and Y denotes a —(CH$_2$)$_{1-2}$— group.

4. A compound according to claim 1, wherein R$^4$ and R$^5$ each independently denote a —O—(CH$_2$)$_{0-2}$-aryl, —(CH$_2$)$_{0-2}$-aryl or heterocyclyl group.

5. A compound according to claim 1, wherein $R^1$ denotes a $C_{1-6}$-alkoxy or —O—($C_{3-7}$)-cycloalkyl group, and $R^4$ and $R^5$ each independently denote a —$(CH_2)_{0-2}$-aryl or heterocyclyl group.

6. A compound according to claim 1, wherein $R^1$ denotes OH or a $C_{1-6}$-alkoxy group.

7. A compound according to claim 1, wherein $R^2$ denotes a $C_{1-6}$-alkyl group, and Y denotes a —$(CH_2)_{1-2}$— group.

8. A compound according to claim 1, wherein $R^1$ denotes OH or a $C_{1-6}$-alkoxy group, $R^2$ and $R^3$ each independently denote a $C_{1-6}$-alkyl group, and Y denotes a —$(CH_2)_{1-2}$— group.

9. A compound according to claim 1, wherein $R^1$ denotes OH, $R^2$ and $R^3$ each independently denote a $C_{1-6}$-alkyl group, X denotes O, and Y denotes a —$(CH_2)_{1-2}$— group.

10. A pharmaceutical composition comprising a pharmaceutically effective amount of a compound according to claim 1, and at least one pharmaceutical carrier or adjuvant.

11. A pharmaceutical composition according to claim 10, wherein said composition is an analgesic composition.

12. A method of preparing a heterocyclic benzocycloalkene compound corresponding to formula I

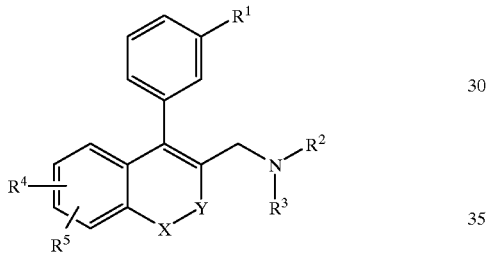

wherein $R^1$ denotes an OH, $C_{1-6}$-alkoxy or —O—($C_{3-7}$)-cycloalkyl group;

$R^2$ denotes a $C_{1-6}$-alkyl group;

$R^3$ denotes a $C_{1-6}$-alkyl, —$CH_2$—CH=C($R^6$)$_2$, or —$CH_2$—($C_{3-7}$)-cycloalkyl group;

$R^4$ and $R^5$ each independently denotes H, Cl, F, $CF_3$, OH, or a $C_{1-6}$-alkyl, OH, $C_{1-6}$-alkoxy, O—($C_{3-7}$)-cycloalkyl, —$(CH_2)_{0-2}$-aryl, α,β- or β,γ—O—$(CH_2)_{1-2}$—O—, —O—$(CH_2)_{0-2}$-aryl, heterocyclyl, α,β- or β,γ-benzo group which is unsubstituted or mono- or disubstituted with F, Cl, $CF_3$, OH, $C_{1-6}$-alkyl, $C_{1-6}$-alkoxy, or —CON($R^6R^7$);

$R^6$ denotes H or a $C_{1-6}$-alkyl group;

$R^7$ denotes H, or a $C_{1-6}$-alkyl, —$(CH_2)_{0-2}$-aryl, or —$CH_2$—($C_{3-7}$)-cycloalkyl group; or $R^6$ and $R^7$ together denote a —$(CH_2)_{5-7}$—, or —$(CH_2)_2$—O—$(CH_2)_2$— group;

X denotes O, S, SO or $SO_2$ and

Y denotes a —$(CH_2)_{1-2}$—, —$CH_2$—C($CH_3$)$_2$—, or —C($CH_3$)$_2$— group; or a pharmaceutically acceptable salt thereof; said method comprising the steps of:

reacting a Mannich base of formula III

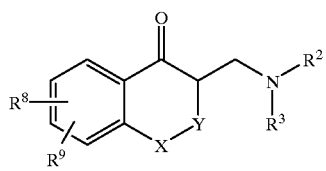

wherein $R^2$, $R^3$, X and Y have the meanings given above, and $R^8$ and $R^9$ have the meanings given above for $R^4$ and $R^5$, respectively, with the exception that any hydroxy function is protected by a benzyloxy or silanyloxy group, with an organometallic compound corresponding to formula IV

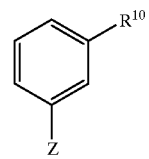

wherein Z denotes MgCl, MgBr, MgI or Li, and $R^{10}$ has the meaning given above for $R^1$, with the exception that any hydroxy function is protected by a benzyloxy or silanyloxy group, to obtain a compound corresponding to formula IIa

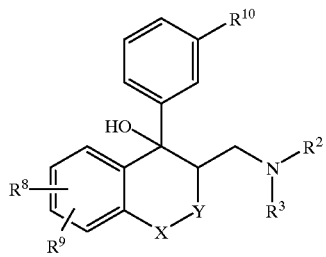

wherein $R^2$, $R^3$, $R^8$ to $R^{10}$, X and Y have the meanings given above; and if any of $R^8$ to $R^{10}$ denotes a protected hydroxy function, converting said compound of formula IIa by removing any hydroxy protective group therein into a tertiary alcohol corresponding to formula II

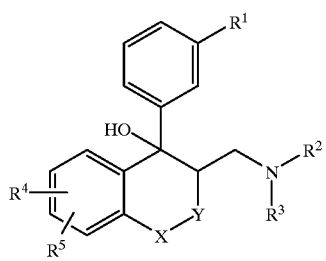

wherein $R^1$ to $R^7$, X and Y have the meanings given above, and reacting said tertiary alcohol corresponding to formula II with acid at a temperature in the range from 0° C. to 100° C. to obtain a compound of formula I.

* * * * *